United States Patent [19]

Colvin et al.

[11] Patent Number: 4,751,466
[45] Date of Patent: Jun. 14, 1988

[54] INSTRUMENT FOR ON-LINE MEASUREMENT OF THE ABSOLUTE ELECTRICAL CONDUCTIVITY OF A LIQUID

[75] Inventors: Alex D. Colvin, Oak Park; James W. Butler, Dearborn Heights, both of Mich.

[73] Assignee: Ford Motor Company, Dearborn, Mich.

[21] Appl. No.: 5,184

[22] Filed: Jan. 20, 1987

[51] Int. Cl.$^4$ ............................................. G01N 27/08
[52] U.S. Cl. ................................. 324/449; 324/444
[58] Field of Search ............... 324/439, 442, 444, 446, 324/448, 449, 450; 307/262

[56] References Cited

U.S. PATENT DOCUMENTS

| | | |
|---|---|---|
| 2,599,413 | 6/1952 | Reichertz . |
| 2,871,445 | 1/1959 | Carter et al. . |
| 3,376,501 | 4/1968 | Peranis . |
| 3,582,767 | 6/1971 | Brum et al. ......................... 324/442 |
| 3,924,175 | 12/1975 | Wilson . |
| 3,993,945 | 11/1976 | Warmoth et al. . |
| 4,118,663 | 10/1978 | Barben, II . |

Primary Examiner—Reinhard J. Eisenzopf
Assistant Examiner—Anthony L. Miele
Attorney, Agent, or Firm—Lorraine S. Melotik; Roger L. May

[57] ABSTRACT

The invention is directed to an instrument for measuring the absolute electrical conductivity of liquids, which instrument may be employed on-line in a recirculating paint bath to measure the conductivity of the paint. The instrument comprises a four electrode probe and a meter which comprises a device for generating and controlling an AC current connected to the first electrode such that a constant AC voltage is maintained across the second and fourth electrodes and a device for measuring and detecting an AC current connected to the third electrode, wherein the fourth electrode is maintained at the same potential as a nearby ground.

6 Claims, 2 Drawing Sheets

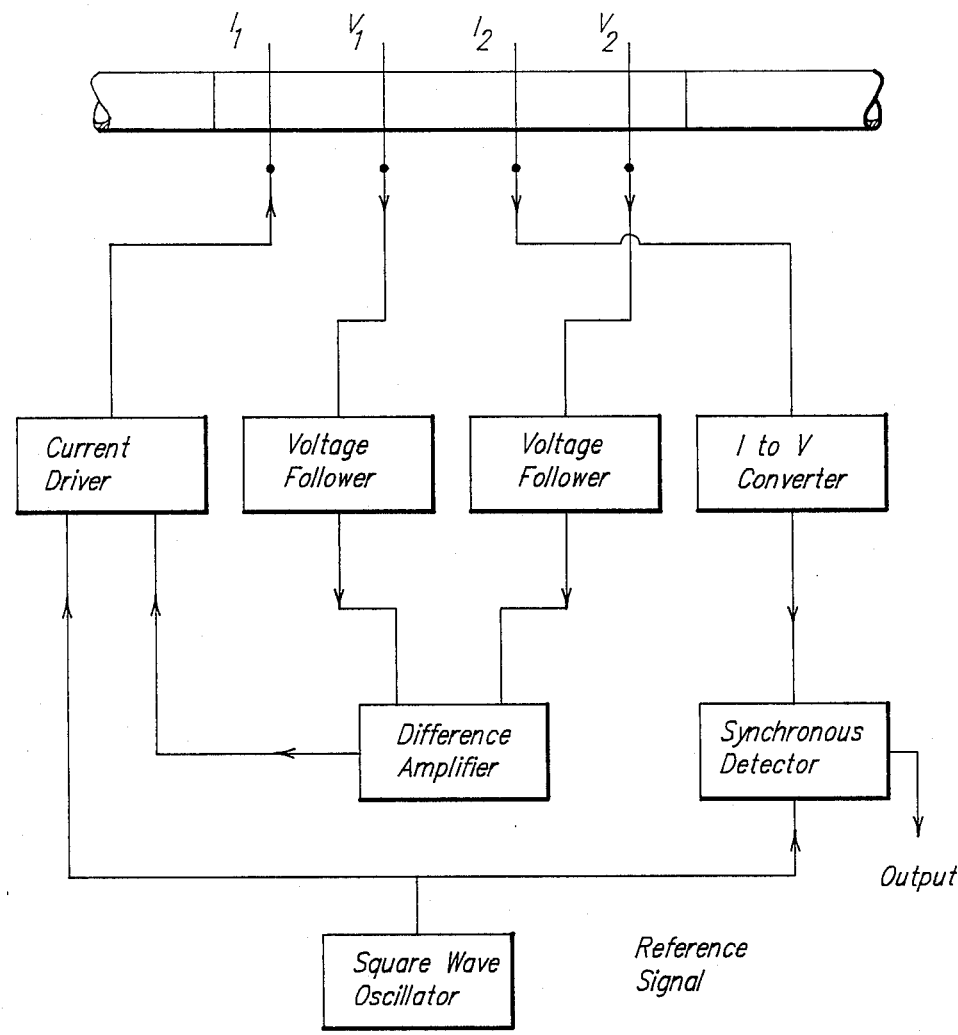
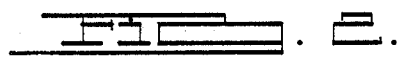

INSTRUMENT FOR ON-LINE MEASUREMENT OF THE ABSOLUTE ELECTRICAL CONDUCTIVITY OF A LIQUID

FIELD OF THE INVENTION

This invention relates to an instrument for measuring electrical conductivity of liquids. More particularly, the invention relates to an instrument capable of being employed on-line with a recirculating liquid to measure its absolute electrical conductivity.

BACKGROUND OF THE INVENTION

The conductivity of a solution is generally monitored using either of two basic methods. One measures conductivity directly by maintaining a fixed voltage between two electrodes immersed in solution so that the resulting current flow is directly proportional to the conductivity. Alternately, the electrodes may be supplied with a constant current flow so that the potential between them is directly proportional to the resistivity of the solution, which is the reciprocal of its conductivity.

Close control of production electrocoat paint conductivity has been found necessary for good paint coverage of a substrate, uniform coating thickness and minimization of pinholes. High conductivity of the paint can cause excessive paint film thickness, pinholes, and a rough uneven surface appearance while low conductivity of the paint can give insufficient paint film thickness and poor "throwing power". Also, if the conductivity of the paint gets too high, ultrafilters can plug, requiring excessive maintenance.

In many applications, a simple two electrode system has sufficed. The use of alternating current of relatively high frequency is preferred for continuous monitoring of the conductivity of a liquid to inhibit the corrosion and buildup of electrolysis products at the electrode surface interface with the solution. Nonetheless, the use of the traditional two electrode conductivity meter, to measure the "batch" conductivity of an electrocoat paint bath, is associated with certain limitations. To make accurate measurements, the electrodes must be cleaned often since the fouling of the electrodes by the buildup of the paint can introduce a substantial impedance across the interface between the electrode metal and the paint solution. This affects the accuracy of the conductivity reading by indicating a much lower conductivity value than is accurate for the paint bath. Such two electrode meters are generally not commercially used on/line, i.e., in a re-circulating paint line. As discussed above, the electrodes would be quickly contaminated by the paint and frequent cleaning, as would be required to make accurate measurements, would necessitate that the paint operation be periodically interrupted to permit inspection and cleaning of the electrodes. However, the alternative to not cleaning the electrodes is error in the conductivity measurement which could have serious adverse consequences for the painting operation and the entire recirculating system.

In order to overcome problems of inaccurate readings due to fouling of two electrode systems, various four electrode systems have been developed. The outer or inner electrodes are current electrodes, generally connected to a source of alternating current, and the other pair of electrodes are voltage electrodes. A cell of this form can be used in either a constant current or a constant voltage mode. However, because negligible current is drawn from the voltage electrodes, even when fouling does occur at all the electrode surfaces resulting in additional impedance at the liquid/electrode interface, the voltage at the voltage electrodes will, within limits, remain unaffected. Thus, with the four probe cell, it is assured that the current corresponds to the voltage at the voltage electrodes, even though the voltage across the current electrodes may increase due to increased impedance arising from fouling.

Reichertz, in U.S. Pat. No. 2,599,413, teaches a constant current meter of this type for measuring the specific electrical resistivity of liquids collected from wells or muds used in connection with drilling. The meter employs four electrodes in a tube having one closed end, the outer electrodes being connected to a source of alternating current and the inner electrodes being voltage electrodes. The circuit includes an AC potentiometer which is balanced by hand, the value of the potentiometer setting at the null being proportional to the resistivity of the liquid. The voltmeter reading is, however, a measure of resistivity, which is inversely proportional to the measured conductivity. The instrument does not give a direct reading of conductivity and this is undesirable. Similarly, Carter et al in U.S. Pat. No. 2,871,445, teach a well fluid resistivity measuring apparatus employing four electrodes in a chamber, whereby the outer electrodes are current electrodes and the inner electrodes are voltage electrodes. The Carter et al invention is taught to be an improvement over the Reichertz invention in that it reads absolute resistivity while the Reichertz meter reads relative resistivity. Nonetheless, these two devices are not suitable for continuous reading of the conductivity of a liquid because repeated hand balancing is needed to obtain the readings.

Peranio, in U.S. Pat. No. 3,376,501, teaches a constant voltage cell for determining the conductivity or salinity of underground water in sand. The cell, which is lowered into the sand, comprises an electrically non-conducting tube having openings (to allow the water in) and four electrodes, the outer electrodes being current electrodes and the inner electrodes being voltage electrodes. Wilson, in U.S. Pat. No. 3,924,175 teaches a DC system for measuring the conductivity of an electrolyte. The use of the DC measurement system is taught by Wilson as being advantageous over AC systems because it does not require a precisely settable and stable high frequency oscillator for generating an a.c. current. It is further taught that polarization is avoided with the use of four electrodes and particular circuitry which allows for an incremental change in current flow between one pair of electrodes to be measured as an incremental change in polarization caused by this current flow. Either the exterior or interior electrodes may serve as reference potential electrodes and respectively either the interior or exterior electrodes pass current for creating the potential. It is taught that preferably the electrodes are arranged in a tube so that a cell constant can be determined, which eliminates the need for calibration of the cell with standardization solutions. However, a deficiency of this system is that changes in the polarization voltage associated with the voltage electrode with time would cause an error in the conductivity measurement. Barben, in U.S. Pat. No. 4,118,663, teaches a four electrode AC conductivity sensor, the inner electrodes being current electrodes and the outer electrodes being voltage electrodes. Also the electrodes may be arranged in other ways in a unitary probe structure. Barben teaches that DC current isolation is provided by certain coupling capacitors, so that the conductivity sensing circuitry is effectively isolated from a DC ground loop that might be established through the recirculation piping to the exterior control circuitry.

All of the above four probe systems have the additional disadvantage that their ability to provide accurate conductivity measurements is adversely affected by nearby AC grounds. Warmoth et al in U.S. Pat. No. 3,993,945 teach that the use of a cell having at least five electrodes allows for the conductivity of liquids, e.g., in kidney dialysis machines, to be measured on-line without error that would be otherwise caused by nearby grounds, e.g., grounded pipe works. This cell includes a tube having first and fourth electrodes which are current electrodes, second and third electrodes, between the first and fourth electrodes, which are voltage electrodes, and the fifth electrode, outside the fourth electrode, for connection to the first electrode and presenting a high impedance to the first electrode and a low impedance to the fifth electrode. Warmoth et al explain that the fourth electrode (a current electrode) is grounded and thus no current will flow between the first and fourth electrodes so that leakage current from the fifth electrode to surrounding grounded pipe works does not affect the conductivity measurement of the liquid.

It is an object of the present invention to provide an instrument having a four electrode probe which can be employed on-line in a recirculating electrocoat paint bath to provide continuous and reliable conductivity readings without the need for electrode cleaning.

It is a further object of the present invention to provide such an instrument for measuring absolute electrical conductivity of a liquid, whose ability to measure the conductivity accurately is not adversely affected by nearby system grounds or conductors. This object requires an instrument in which the flow of electrical current from the electrodes, for example to grounded metal pipe work connected to the probe, is thus inhibited or not counted in the measurement of the conductivity of the liquids.

It is still a further object of the invention to provide such an instrument which is able to measure the absolute conductivity of a liquid without the need for conductivity standard solutions to calibrate the instrument.

DISCLOSURE OF THE INVENTION

The invention is directed to an instrument for measurement of the absolute electrical conductivity of a liquid, i.e., without need for the use of a reference solution to calibrate the instrument. The instrument comprises (A) a probe comprising an electrically insulating tube and four electrodes within the tube, which electrodes are spaced substantially parallel to each other and substantially perpendicular to the longitudinal axis of the tube, forming a second and third electrode between a first and fourth electrode, which tube has substantially uniform cross-sectional area at least between the second and third electrodes, and (B) a meter which comprises means for generating and controlling an AC current connected to the first electrode such that a constant AC voltage is maintained across the second and fourth electrodes and means for measuring and detecting an AC current connected to the third electrode, wherein the fourth electrode is maintained at the same potential as the nearest ground.

Preferably, the means connected to the third electrode comprises a synchronous detection means for measuring the current. Preferably, the voltage across the second and fourth electrodes is a square wave voltage.

Advantageously, since the present invention instrument comprises four electrodes and uses AC current, it can be employed on-line in a recirculating electrocoat paint bath to provide continuous and reliable readings of absolute conductivity without the need for electrode cleaning.

Advantageously, it is a characterizing aspect of the present invention instrument that it can be used near system grounds and conductors while still giving accurate conductivity readings. It is based on the particular arrangement of the electrodes of the instrument, whereby the third electrode, which is used to measure current, is shielded by the fourth electrode which is a voltage electrode, and whereby the fourth electrode is at the potential of the system ground, i.e., the nearest ground. Because the fourth electrode is at the system ground, current is not passed (lost) from the third electrode to the fourth electrode or a neighboring ground. Additionally, the second electrode, a voltage electrode, is shielded by the first electrode, the electrode at which the current is generated, and since the current at the first electrode is not measured (i.e., only the current at the third electrode is measured), no error is made in conductivity measurements if some of the generated current goes (is lost) from the first electrode to a nearby system ground.

Still another characterizing aspect of the present invention instrument is that it is capable of measuring the absolute conductivity of a liquid, i.e., it does not require calibration with a standard solution of known conductivity prior to being employed to measure on-line liquid conductivity. This feature of the invention is attained by employing the electrodes in the defined configuration, and in a tube, i.e., substantially parallel to each other and substantially perpendicular to the longitudinal axis of the tube, so that knowing the distance between the second and third electrode, the cross-sectional area of the insulating tube between the second and third electrodes, and the conductance factor of the circuit which is rapidly determined, a calibration constant for the instrument can be calculated. This calibration constant can thereafter be used with the voltage output reading to calculate conductivity without the use of standard conductivity solutions, as is necessary with prior art measuring conductivity instruments. Measurement of conductivity with the present invention instrument is not dependent on electrode area or the electrode material.

DESCRIPTION OF THE DRAWINGS

FIG. 2 shows the preferred embodiment of FIG. 1 by means of a simplified block diagram.

DESCRIPTION OF THE PREFERRED EMBODIMENT

Figure 1:
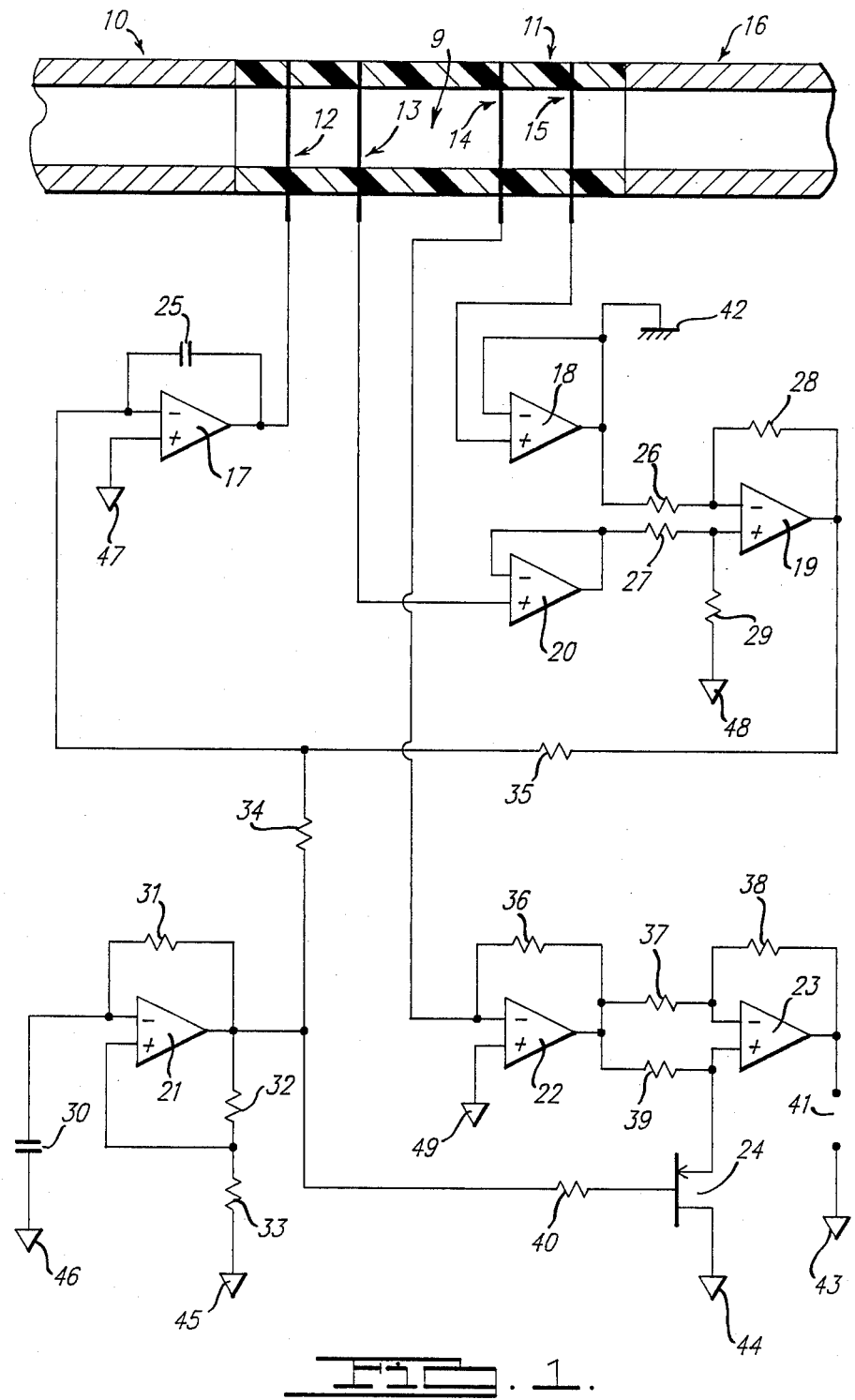
FIG. 1 is a schematic diagram illustrating a preferred embodiment of the instrument of this invention comprising a probe and meter means for measuring electrical conductivity of a liquid, the instrument being employed on-line with a circulating liquid whose electrical conductivity is being measured.

The conductivity instrument of this invention comprises a probe capable of being connected on-line with grounded metal pipes and a meter for determining the absolute conductivity of a liquid which passes through the probe. The ability of the instrument to give accurate readings is virtually not affected when the probe is connected on-line with grounded metal pipes. While the instrument of this invention finds particularly advantagous use when being connected on-line with circulating liquids, it may also be employed for "batch" measuring as well as in other ways, for example, in a pipette (which functions as the tube of the probe of this invention) with a bulb at one end to draw up the liquid to be measured. Additionally, while the instrument of this invention has been discussed as useful for measurement of the absolute conductivity of electrocoat paints, its use is not limited thereto. It may be used for measuring the absolute conductivity of any solution, e.g., tap water, cooling fluid, battery acid and alcohol fuel, as would be apparent to one skilled in the art in view of the present disclosure.

The invention will now be described by way of example with reference to the accompanying drawings, in which FIG. 1 is a schematic view, partly in cross-section, illustrating the construction of a preferred embodiment of an electrical conductivity measuring instrument according to this invention. The flow-through probe is shown in FIG. 1 and comprises an electrically non-conducting tube (11) enclosing four electrodes. The four electrodes are spaced substantially parallel to each other and substantially perpendicular to the longitudinal axis inside the tube. The spacing between the electrodes is not critical, i.e., it may be of any convenient spacing, but preferably is at least equal to the inside diameter of the tube. When measuring very conductive liquids with the instrument of this invention, even larger spacing is desirable. As described above, it is only the cross-sectional area of that portion of the tube (11) between the inner two electrodes (13) and (14) which needs to be substantially uniform. In general practice, for commercial convenience the cross-sectional area of the entire probe tube would generally be substantially uniform. The tube can be composed of any non-conducting (electrically insulating) material, e.g., plastic, such as polyvinyl chloride, glass, or rubber. In this figure, the tube (11) is connected between metal pipes (10) and (16) carrying liquid (9) whose electrical conductivity is being measured by means of the instrument of this invention. Two electrodes (12) and (14) are used to pass current, while two electrodes, (13) and (15), are use to measure the voltage. These electrodes may be made of any numerous materials, known to those in the art, used to make electrodes, e.g., stainless steel, brass, and platinum, the latter being often used in conductivity meters. The choice of optimal electrode material will be dependant, in part, on the composition of the solution whose conductivity is being measured. The electrodes may be of varying shape, e.g., rectangular, square or needle like and may even be "bolts" as were employed by Applicants in embodiments of this invention. While the electrodes in FIG. 1 are depicted as going across the diameter of the tube, it is not necessary that the electrodes extend from one side of the tube to the other side. It is only necessary that such protruding electrodes extend a fraction of the way across the tube diameter. Additionally, the electrodes may consist of longitudinally spaced rings co-axial with the tube as shown, for example, in U.S. Pat. No. 3,993,945, the teachings relative such ring electrodes being hereby expressly incorporated by reference. The inner surfaces of such electrodes would more preferably be disposed flush with and contiguous with the inner surface of the tube.

In FIG. 1, current electrode (12), by means of which current is supplied, but not measured, is seen to be at one end of tube (11). The current at electrode (12) is not measured and therefore any current lost to a nearby ground, e.g., metal pipe (10) adds no error to the conductivity measurement. The current at electrode (12) is depicted in FIG. 2 as $I_1$. Adjacent to current supplying electrode (12) is a voltage measuring electrode (13). A voltage, $V_1$, depicted in FIG. 2, is measured at voltage measuring electrode (13). The third electrode is a current measuring electrode (14). The current at electrode (14) is depicted in FIG. 2 as $I_2$. The fourth electrode (15) measures the voltage surrounding current measuring electrode (14). A voltage, $V_2$, shown in FIG. 2 is measured at electrode (15). As discussed above, the voltage measuring electrode (15) is maintained at the same potential as a nearby ground, e.g., a building or plumbing ground (42), as shown in FIG. 1. This may be done by attaching the low impedence output of buffer amplifier (18), which measures the voltage at electrode (15), to building or plumbing ground (42). Electrodes (14) and (15) are thereby shielded from any ground currents and thus the current due to electrical conduction by the paint is correctly measured.

As taught above, the meter of this invention instrument comprises means for generating and controlling an AC current connected to the first electrode, such that a constant AC voltage is maintained across the second and fourth electrodes, and means for measuring and detecting an AC current connected to the third electrode. As would be apparent to one skilled in the art in view of the present disclosure, many such means are available and known to those skilled in the art. Generally in this type of circuitry, generated current is driven into a current electrode, suitably from a voltage controlled generator. The voltage measured across the voltage electrodes is dependent upon the current from the generator and the conductivity of the liquid contacting the electrodes. This voltage is sensed by a high input impedance amplifier, the output of which is supplied to a comparator where the signal is compared with a reference signal. The output of the comparator is applied to the voltage controlled generator output in such a manner as to drive current through the current electrodes of a magnitude to maintain a constant voltage at the voltage electrodes. The driven current under such circumstances is directly proportional to the electrical conductivity of the liquid.

A preferred embodiment of the meter of the instrument of this invention is shown schematically in FIG. 1 and in block form FIG. 2. As would be apparent to one skilled in the art, the block diagram shown in FIG. 2 is a simplified representation of the probe and meter of FIG. 1. This meter comprises means to generate and control an AC current, such that a constant AC voltage is maintained, and means to measure and detect an AC current. As can be seen from FIG. 1, the constant voltage generator circuit comprises a constant (reference) a.c. oscillator amplifier (21), i.e., an oscillator which generates a fixed amplitude wave, preferably a square wave, and preferably operating at approximately 1

KHz, resistors (31), (32) and (33) and capacitor (30). Resistor (31) connects the inverting input of amplifier (21) to the output of amplifier (21). Resistor (32) connects the output of amplifier (21) to the non-inverting input of amplifier (21). Resistor (33) connects the non-inverting input of amplifier (21) to circuit ground (45). Capacitor (30) connects the inverting input of amplifier (21) with circuit ground (46). The square wave oscillator shown in FIG. 2 comprises oscillator amplifier (21), the resistors (31), (32), and (33) and capacitor (30).

In FIG. 1, the voltage at electrode (13) is buffered by the unity gain operational amplifier (20). The voltage at electrode (15) is buffered by the unity gain operational amplifier (18). Amplifiers (18) and (20) are shown in FIG. 2, as the voltage followers associated with $V_2$ and $V_1$, respectively. The output of amplifier (18) is connected to a ground (42) e.g., a plumbing ground, which acts as a shield for electrode (15). The two buffered outputs from amplifiers (18) and (20) are subtracted using amplifier (19) and its associated resistors (26), (27), (28) and (29). Resistor (26) connects the output of amplifier (18) and the inverting input of amplifier (19). Resistor (27) connects the output of amplifier (20) to the non-inverting input of amplifier (19). Resistor (28) connects the output of amplifier (19) to the inverting input of amplifier (19). Resistor (29) connects the non-inverting input of resistor (29) to circuit ground (48). Amplifier (19) and its associated resistors are shown in FIG. 2 as the difference amplifier.

The outputs of difference amplifier (19) and oscillator amplifier (21) are summed in the current driver amplifier (17). Resistor (35), which is connected the output of amplifier (19), and resistor (34), which is connected to the output of oscillator amplifier (21), are connected to the inverting input of amplifier (17), which controls the current between the current electrodes (12) and (14) so as to produce a fixed fraction of the (preferably, square wave) voltage between the two voltage sensing electrodes (13) and (15). Resistors (34) and (35) are preferably proportioned so as to keep the peak to peak voltage between electrodes (13) and (15) at about 1.5 volts. A lower voltage could reduce the sensitivity of the apparatus while a higher voltage could cause bubbles to form on the current electrodes (12) and (14). The non-inverting input of amplifier (17) is attached to circuit ground (47). Capacitor (25) is connected between the output of amplifier (17) and its inverting input to provide stability and avoid high frequency oscillations. Amplifier (17), capacitor (25), and resistors (34) and (35) are shown in FIG. 2 as the current driver. The output of amplifier (17) supplies current to current electrode (12). The current passing into electrode (14) goes to amplifier (22) which is a current to voltage converter. The current sampling resistor (36) is connected between the inverting input of amplifier (22) and the output of amplifier (22). The output of amplifier (22) is the AC voltage representing the conduction current, i.e., the current of conductive liquid (9) whose electrical conductivity is being measured.

The synchronous detector shown in FIG. 2 is made up of amplifier (23), resistors (37), (38), (39), field effect transistor switch (24) and its input limiting resistor (40). The switch (24) grounds and floats the non-inverting input of amplifier (23). This provides a gain of $-1$ when the non-inverting input is grounded to (44) and a gain of $+1$ when the non-inverting input is floated. The alternating gain provides detection synchronized with the oscillator amplifier (21). The output at (41) is the circuit output of the synchronous detector and its voltage is proportional to the solution conductivity being measured. A circuit ground (43) is provided. The use of the synchrous detector (23) reduces electrical pickup, eliminates any electrode polarization and eliminates effects due to DC currents passing through the probe. It is not required, however, for current detection. Alternately, any AC to DC converter or detector can be used, as would be apparent to one skilled in the art in view of the present disclosure.

With this instrument, an absolute conductivity measurement can be made without first calibrating with a known conductivity solution, because the current path in the measured liquid is limited by the cross-sectional area of the non-conducting tube between the second and third electrodes. The calibration constant for the probe is equal to this inside cross-sectional area of the tube divided by the distance between the second and third electrodes multiplied by the conductance factor of the circuit, which is easily obtained as described hereinafter. This system can provide absolute conductivity measurements from the following formulas, which defines the relationship between the physical parameters and the conductivity to be measured: $K = C\ V$ where $C = F\ L/A$ and where:

K = absolute conductivity being measured (in micromhos/cm)
F = conductance factor of the circuit (in micromhos/volt)
V = circuit output voltage (in volts)
L = distance between the second and third electrodes (in cm).
A = inside cross-sectional area of the insulating tube between the second and third electrodes (13) and (14) (in cm$^2$).

Using the meter of this invention, the conductance factor (F) of the circuit is easily measured by attaching the leads from electrodes (13) and (12) to one end of a known resistor and attaching the leads from electrodes (14) and (15) to the other end of the resistor. The zero conductance point, as read by the meter, can be determined by disconnecting the resistor. (The conductance of a resistor is the reciprocal of the actual resistance value.) The meter output voltage is linear with respect to conductance. Therefore, only one calibration point is needed in addition to a zero conductance point. The conductance factor (F) is then obtained from $F = A/(VLR)$, where R is the known resistance value (i.e., of the known resistor) giving a meter output voltage V.

In order to demonstrate the absolute measurement capability of the present invention apparatus, a standard conductivity solution was measured. The conductance of the standard solution (Yellow Springs Instrument Co., conductivity standard YSI 3160, 1000 micromhos/cm) was measured using the instrument shown in FIG. 1. The internal diameter of the tube is 2.38 cm, and the distance between the two center electrodes is 7.62 cm. The temperature of the solution was 22.8° C. The resistor substituted for equal circuit output was 1808 ohms. Correcting for temperature (2%/°C.), a corrected measured value of 989 micromhos/cm was measured for the 1000 micromho/cm standard. The 1.1% conductivity difference is well within experimental error.

Testing was also carried out to determine the long term ability of this instrument to accurately and continuously monitor the electrical conductivity of a production electrocoat paint bath. This is a good test situation, because the electrodes are easily fouled by the paint. Electrode fouling of conventional two electrode conductivity meters (which meters are commercially used to measure the electrical conductivity of paint baths) would, as discussed above, lead to erroneous measurements. This testing consisted of comparing the electrical conductivity readings made twice daily directly of the electrocoat paint bath with an instrument according to this invention with those made directly with a conventional two probe electrode batch conductivity meter. Still further, for comparison with the present invention apparatus and batch meter readings, independent electrical conductivity measurements were made in the laboratory of paint samples periodically (weekly) removed from the paint bath. The present instrument probe used in these tests comprised a plastic tube of 2.38 cm diameter with four stainless steel electrodes (bolts which extended across the entire diameter of the tube). The tube was installed parallel to the vertical pipe between the paint feed pump and the static mixers, i.e., in the arrangement shown in FIG. 1. The cathodic electrocoat paint employed in this test is pumped at a rate of approximately 10 feet/second through the tube. The meter is equipped with an error indicating light which activates if any electrode does not make proper electrical contact with the electrocoat paint. The probe of the instrument of this invention was always in the flowing paint stream and was never cleaned. The monitor was originally calibrated to agree with the batch meter, which was cleaned before each reading, and subsequent readings were made over a period of many months. Conventional conductivity (batch) meters have platinum electrodes which easily foul and thus need special attention and calibration. In contrast, the instrument according to this invention required no additional care or maintenance during the extended period of the test.

After the initial calibration, the readings given by the instrument of this invention were more consistent with the laboratory determined values than those recorded by the in plant batch conductivity meter, which (batch) readings were generally lower than those obtained by either the present invention instrument or the laboratory evaluations, and had larger fluctuations. The readings of the instrument of this invention were more consistant with those determined independantly in the laboratory.

In view of this disclosure, many modifications of this invention will be apparent to those skilled in the art. It is intended that all such modifications which fall within the true scope of this invention be included with the terms of the appended claims.

We claim:

1. An instrument for measuring of the absolute electrical conductivity of a liquid, said instrument comprising:

a probe comprising an electrically insulating tube and four electrodes within said tube, said electrodes being spaced substantially parallel to each other and substantially perpendicular to the longitudinal axis of said tube so as to form a second and third electrode between a first and fourth electrode, said tube having a substantially uniform cross-sectional area at least between said second and third electrodes; and a meter comprising:

means for generating and controlling an AC current connected to said first electrode such that a constant AC voltage is maintained across said second and said fourth electrodes; and means for measuring and detecting an AC current connected to said third electrode; wherein said fourth electrode is maintained at ground potential.

2. An instrument according to claim 1, wherein the measuring and detecting means connected to said third electrode comprises a synchronous detection means for measuring the current.

3. An instrument according to claim 2, wherein said synchronous detection means comprises a field effect transistor switch which is driven by a square wave oscillator.

4. An instrument according to claim 1, wherein said generating and controlling means connected to said first electrode generates a square wave voltage.

5. An instrument according to claim 1, wherein said electrodes are spaced at least one tube diameter apart from one another.

6. An instrument according to claim 1, wherein said constant AC voltage is a voltage of about 1.5 volts peak to peak.

* * * * *